United States Patent [19]

Cameron

[11] 4,421,611

[45] Dec. 20, 1983

[54] ACETYLENIC COMPOSITIONS AND NICKEL PLATING BATHS CONTAINING SAME

[75] Inventor: James C. Cameron, Lakewood, Ohio

[73] Assignee: McGean-Rohco, Inc., Cleveland, Ohio

[21] Appl. No.: 431,102

[22] Filed: Sep. 30, 1982

[51] Int. Cl.$^3$ .................... C25D 3/16; C25D 3/56; C07C 33/04

[52] U.S. Cl. .................... 204/43 T; 204/49; 562/538; 562/579

[58] Field of Search ............... 562/538, 579; 204/49, 204/43 T, 112, 123, DIG. 2

[56] References Cited

U.S. PATENT DOCUMENTS

| | | | |
|---|---|---|---|
| 2,841,602 | 7/1958 | Brown et al. | 204/49 X |
| 3,378,470 | 4/1968 | Kroll | 204/49 |
| 3,515,652 | 6/1970 | Law | 204/49 |
| 4,002,543 | 1/1977 | Clauss et al. | 204/41 |
| 4,077,855 | 3/1978 | Popescu | 204/49 |
| 4,101,387 | 7/1978 | Creutz et al. | 204/43 T |

FOREIGN PATENT DOCUMENTS

| | | | |
|---|---|---|---|
| 951811 | 11/1956 | Fed. Rep. of Germany | 562/538 |
| 871276 | 2/1959 | United Kingdom | 204/49 |

OTHER PUBLICATIONS

F. Degering et al., "Organic Chemistry", p. 34, *College Outline Series*, 6th Ed., Barnes & Nobel, Inc., (1951).
John D. Roberts et al., "Basic Principles of Organic Chem.", p. 216, (1965).

*Primary Examiner*—G. L. Kaplan
*Attorney, Agent, or Firm*—Maky, Renner, Otto & Boisselle

[57] ABSTRACT

A new acetylenic composition, 3-(2-propynoxy)-2-propenoic acid, and its methods of preparation are described. Also, acetylenic compositions are described which are prepared by the process which comprises the steps of (a) reacting propargyl alcohol with an alkali metal permanganate in an aqueous alkaline solution,
(b) filtering the reaction mixture, and
(c) acidifying the filtrate with acid. The acetylenic compositions prepared in this manner are useful in aqueous acidic plating baths for the electrodeposition of a bright nickel or nickel-iron alloy on a substrate. Methods for the electrodeposition of nickel and nickel-iron alloys from such baths as well as additive compositions for forming the baths are described.

32 Claims, No Drawings

ACETYLENIC COMPOSITIONS AND NICKEL PLATING BATHS CONTAINING SAME

BACKGROUND OF THE INVENTION

This invention relates to new acetylenic compositions and to the use of such compositions in plating baths for the electrodeposition of nickel and nickel-iron alloys.

Aqueous acidic plating baths for producing nickel coatings on substrates have been known in the art, and most nickel plating baths are based on the use of a standard Watts-type bath which includes nickel sulfate, nickel chloride and boric acid dissolved in water. Various additives have been incorporated into the Watts-type baths to improve the quality of the coatings.

Methods for producing nickel-iron alloys on substrates also have been described in the art, and similarly, most of the nickel-iron plating baths are based on the use of standard Watts-type baths to which has been added ferrous sulfate. Many additives also have been suggested as being useful in such nickel-iron plating baths, and the present invention relates to the discovery that the quality of the deposits derived from such nickel and nickel-iron plating baths can be improved by incorporating therein novel acetylenic compositions as described hereinafter.

Modern processes as described in the prior art relating to the use of the Watts-type bath are generally used in conjunction with additive systems which comprise brighteners known as Class I brighteners which include compositions such as bath-soluble sulfinic acids, sulfonic acids, sulfonamides, sulfonimides, sulfimides and the water-soluble salts of these materials. The plating baths also can and generally will contain Class II brighteners which generally are unsaturated organic materials which will produce the leveling and increase the luster of deposit when used in conjunction with the Class I brighteners. Typical Class II brighteners for nickel plating baths are acetylenic or ethylenic alcohols, ethoxylated and propoxylated acetylenic alcohols, coumarins, aldehydes, and compounds containing the C≡N linkage.

The use of acetylenic compositions as brighteners for nickel and nickel-iron plating baths has gained wide acceptance and has been described in many patents. Various acetylenic-containing compositions have been suggested including acetylenic amines, acetylenic alcohols, acetylenic esters, acetylenic sulfonic acids and sulfonates and alkoxylated acetylenic alcohols and amines. Illustrative of the patents describing the use of acetylenic derivatives as brighteners in nickel and nickel-iron plating baths include the following U.S. Pat. Nos. 3,133,006; 3,140,988; 3,152,975; 3,160,574; 3,170,853; 3,305,462; 3,366,557; 3,699,016; 3,378,470; 3,502,550; 3,515,652; 3,711,384; 3,719,568; 3,723,260; 3,759,803; 3,795,592; 3,860,638; 3,862,019; 3,844,773; 3,898,138; 3,907,876; 3,969,198; 4,054,495; 4,062,738.

SUMMARY OF THE INVENTION

It now has been found that novel acetylenic compositions can be prepared by the process comprising the steps of
 (a) reacting propargyl alcohol with an alkali metal permanganate in an aqueous alkaline solution,
 (b) filtering the reaction mixture, and
 (c) acidifying the filtrate with acid. The composition prepared by the above process contains principally unreacted propargyl alcohol and 3-(2-propynoxy)-2-propenoic acid, a new compound. This compound also can be prepared by the reaction of propargyl alcohol with propiolic acid.

The novel acetylenic compositions of this invention can be utilized as brightening and leveling agents in nickel and nickel-iron electroplating baths.

DESCRIPTION OF THE PREFERRED EMBODIMENTS

A novel acetylenic composition has been prepared. The compound has been identified as 3-(2-propynoxy)-2-propenoic acid having the general formula

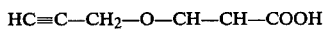

This compound can be prepared and isolated essentially pure or can be obtained as a principal ingredient in a mixture of acetylenic components. One method of preparing the above-identified propenoic acid comprises reacting propiolic acid with propargyl alcohol in an aqueous alkaline solution, and thereafter acidifying the reaction mixture. Various alkaline solutions can be utilized including sodium hydroxide or potassium hydroxide in water. Acidification of the reaction mixture upon completion of the reaction can be effected with mineral acids such as sulfuric acid.

The following example illustrates the method of preparing 3-(2-propynoxy)-2-propenoic acid.

EXAMPLE 1

Propiolic acid (five grams) is diluted with water to 50 ml., and three grams of sodium hydroxide is added. A propargyl alcohol solution is prepared from four grams of propargyl alcohol diluted to 100 ml. with water followed by the addition of one gram of sodium hydroxide. This propargyl alcohol solution is added to the propiolate solution while maintaining a temperature at about 60°–80° C. The mixture is maintained at this temperature for approximately two hours whereupon the solution is acidified with sulfuric acid to a pH of about 3.

The solution is extracted with five 100 ml. portions of ethyl ether. The ether layer is dried over sodium sulfate followed by stripping of the ether. The residue which remains consists of a solid and a yellow liquid. The residue is washed with chloroform and filtered leaving a white solid. The melting point of the solid which is the desired product is 115°–119° C.

The acetylenic compositions of the invention also are prepared by the process which comprises the steps of
 (a) reacting propargyl alcohol with an alkali metal permanganate in an aqueous alkaline solution,
 (b) filtering the reaction mixture, and
 (c) acidifying the filtrate with acid.

The precise nature of the composition is not known with certainty, but analysis of the product of this reaction indicates that the composition is made up principally of unreacted propargyl alcohol and 3-(2-propynoxy)-2-propenoic acid. The propenoic acid can be recovered from the reaction product by extracting with chloroform.

The reaction of the propargyl alohol with the alkali metal permanganate is conducted in aqueous alkaline solution. Generally, the pH of the solution will be maintained within the range of from about 9 to about 12, and more preferably at about a pH of 11. The desirable pH can be attained by dissolving an alkaline material such as an alkali metal hydroxide in water. Preferred alkali metal hydroxides are a sodium hydroxide and potassium hydroxide.

The alkali metal permanganates which are particularly useful in the preparation of the acetylenic composition of the invention are potassium permanganate and sodium permanganate, although potassium permanganate is preferred. The amount of permanganate utilized in the preparation of the acetylenic compositions of the invention can be varied over a wide range although amounts of from about 0.10 to about one part of permanganate for every part of propargyl alcohol are preferred. More preferably, from about 0.15 to about 0.50 parts of permanganate is utilized per part of propargyl alcohol. The concentration of propargyl alcohol and alkali metal permanganate in the aqueous solution similarly is not critical although a concentration of propargyl alcohol in the reaction mixture of from about one to about 40% by volume is preferable.

The aqueous alkaline reaction mixture is heated to effect a reaction, and, generally, the reaction is completed in about one to two hours or less. Although higher temperatures may be utilized, the reaction temperature is generally maintained below about 90° C. Although the sequence of addition does not appear to be critical, in one embodiment, it is preferred to add the alkali metal permanganate and sodium or potassium hydroxide pellets to the desired amount of water and thereafter add the propargyl alcohol either neat or dissolved in water.

Upon completion of the reaction, the reaction mixture is filtered to remove the solid material present which is principally manganese dioxide. The filter cake can be washed with water to remove final traces of entrapped reaction product.

The filtrate is acidified by the addition of an inorganic acid such as sulfuric acid to a pH of 2 or less, and generally to a pH of about 1.5. The acidified aqueous filtrate is the desired acetylenic composition. As mentioned above, the precise nature of the acetylenic compositions prepared in accordance with the method of the invention is unknown although the composition does appear to comprise a mixture of acetylenic compounds containing some unreacted propargyl alcohol and 3-(2-propynoxy) 2-propenoic acid.

The following examples illustrate the preparation of the acetylenic compositions of the invention utilizing the permanganate process. Unless otherwise indicated, all parts and percentages are by weight.

EXAMPLE 2

A mixture of 1.5 parts of propargyl alcohol, 0.36 parts of potassium permanganate and about one part of sodium hydroxide is prepared in sufficient water to provide a total of about 50 parts of reaction mixture. The pH of this reaction mixture is about 11. The mixture is heated to a temperature of about 90° C. and maintained at this temperature for about one hour whereupon the reaction mixture is filtered. The filtrate is acidified with sulfuric acid to a pH of about 1.5, and the desired acetylenic composition is obtained as an aqueous solution.

EXAMPLE 3

The procedure of Example 2 is repeated except that the potassium permanganate is replaced by an equivalent amount of sodium permanganate.

EXAMPLE 4

The procedure of Example 2 is repeated except that the sodium hydroxide is replaced by an equivalent amount of potassium hydroxide.

EXAMPLE 5

A mixture of 30 parts of propargyl alcohol, 3.6 parts of potassium permanganate and about one part of sodium hydroxide is prepared in sufficient water to provide about 100 parts of reaction mixture. The pH of this reaction mixture is about 11. The mixture is heated to a temperature of about 60° C. and maintained at this temperature for about one hour whereupon the reaction mixture is filtered. The filtrate is acidified with sulfuric acid to a pH of about 1.5, and the desired acetylenic composition is obtained as an aqueous solution.

EXAMPLE 6

The procedure of Example 5 is repeated except that the potassium permanganate is replaced by an equivalent amount of sodium permanganate.

EXAMPLE 7

The procedure of Example 6 is repeated except that the sodium hydroxide is replaced by an equivalent amount of potassium hydroxide.

The acetylenic compositions of the invention such as those described above are useful additives in conventional nickel and nickel-iron electroplating baths, and when present in such baths, result in a bright and level nickel or nickel-iron alloy deposit. When the compositions of the invention are utilized in conventional nickel and nickel-iron alloy plating baths wherein other conventional additives are included such as surfactants and Class I brighteners, the deposits obtained by such baths are fully bright and level over a wide curent density range including the low current density areas.

The conventional nickel plating baths generally contain at least one nickel salt such as nickel sulfate, nickel chloride and nickel sulfamate. In addition to the nickel salts, the plating baths also generally contain boric acid. Basic nickel plating baths of this type are known as the Watts-type nickel plating baths. Ferrous iron may be added to the nickel plating baths as ferrous sulfate, ferrous chloride or ferrous sulfamate. The sulfate generally is preferred because of costs and purity.

When nickel sulfate salts are used as a source of nickel ions, the sulfates normally are present in amounts ranging from about 150 to about 450 grams/liter (calculated as nickel sulfate hexahydrate). Nickel chloride often is used in combination with the sulfates and may be present in an amount ranging from about 10 to about 200 grams/liter (calculated as nickel chloride hexahydrate). The chloride or halide ions are included in the plating bath to obtain satisfactory conductivity of the solution and to improve anode dissolution by reducing polarization.

Boric acid normally is included in the nickel and nickel-ion alloy plating baths since it is useful in the formation of smooth deposits and is believed to have a cooperative effect with the supplemental leveling agents. Boric acid also has been suggested as being useful as a weak buffer to control the pH of the cathode film. The concentration of boric acid in the bath is not critical, and generally will be in the range of from about 10 to about 60 grams/liter. When present, the inorganic salts of iron may be present in an amount ranging from about 3 to about 50 grams/liter, the amount of iron ions present being determined by the amount of nickel ions present and the desired ratio of nickel:iron in the coating deposited on the substrate.

Lower salt containing nickel plating baths also are improved by this invention. In such baths, nickel sulfates generally are present in amounts of from 60 to 125 grams/liter calculated as nickel sulfate hexahydrate, and nickel chloride will be present in larger amounts such as 75–200 grams/liter calculated as nickel chloride hexahydrate.

The amount of acetylenic compositions of the present invention which is incorporated into the baths improve the level and brightness of the nickel and nickel-alloy deposits is an amount which is effective to accomplish the desired improvement in brightness and leveling. When the acetylenic compound is 3-(2-propynoxy)-2-propenoic acid, the amount including in the plating baths of the invention will range from about 0.001 to about 0.05 grams/liter. In general, the amount of acetylenic composition of the type represented by Examples 2 through 7 included in the plating baths of the invention will be from about 0.01 to about one gram of total reaction product per liter and more generally from about 0.01 to about 0.5 grams per liter of bath.

The properties of the nickel and nickel-iron coatings deposited by the baths of the invention may be enhanced further by including in the bath, from about 1.5 to about 10 grams per liter of at least one brightening agent normally used in nickel and nickel-iron plating baths. These brighteners include bath-soluble sulfinic acids, sulfonic acids, sulfonamides, sulfonimides, sulfimides, and the water-soluble salts of these materials. Examples of such brighteners include the alkyl naphthalene and benzene sulfonic acids, the benzene and naphthalene di- and trisulfonic acids, benzene and naphthalene sulfonamides, and sulfonimides such as saccharin, vinyl and allyl sulfonamides and sulfonic acids. Specific examples of such brighteners include Sodium saccharinate
Trisodium 1,3,6-naphthalene trisulfonic acid
Trisodium 1,3,7-naphthalene trisulfonic acid
Benzene sulfinic acid
Sodium styrene sulfonate
p-toluene sulfinic acid
p-toluene sulfonic acid
Ditolylsulfimide
Sodium salt of di-o-tolyl disulfimide,
Sodium salt of dibenzene disulfimide
Pyridine-3-sulfonic acid
p-vinylbenzene sulfonic acid
Sodium allyl sulfonate
Sodium vinyl sulfonate
Sodium propargyl sulfonate The above brightening agents illustrate the class known as Class I brightening agents. More comprehensive listings of such brighteners may be found in the art such as in U.S. Pat. No. 3,922,209 which patent hereby is incorporated by reference.

The plating baths of this invention also may contain additional compounds which have been classified in the art as Class II brighteners. The Class II brighteners generally are unsaturated, organic materials which produce the leveling and increase the luster of the deposit when used in conjunction with the Class I brighteners. Typical secondary brighteners are acetylenic or ethylenic alcohols, ethoxylated and propoxylated acetylenic alcohols, coumarins, aldehydes, and compounds containing the $C \equiv N$ linkage. Specific examples of such brighteners include: ethoxylated butynediol; 2-butyne-1,4-diol; propargyl alcohol; thiodipropionitrile; and ethoxylated propargyl alcohol.

A particularly preferred type of secondary brightener useful in the plating baths of the invention is represented by the following generic Formula I $$R_1C \equiv CCH_2OR_2 \qquad \text{I}$$

wherein $R_1$ is selected from H, $CH_2OH$, $CH_2OR_2$; $R_2$ is selected from H, $(CH_2CH_2O)_nH$, $(CH_2CH(OH)CH_2)_nH$, $(CH_2)_mSO_3M$, $(CH_2CH(OH)CH_2)_n$—$SO_3M$, $(CH_2CH_2O)_n(CH_2CH(OH)CH_2)SO_3M$, and $(CH_2CH_2O)_n(CH_2)_mSO_3M$, where n is an integer from 1 to 10; m is an integer from 1 to 4; and M is selected from hydrogen, ammonium, alkali metal, nickel and cobalt. These compounds are the lower molecular weight acetylenic alcohols (more specifically propargyl alcohol and butyne diol) and their epoxide adducts, their sulfonated adducts, and their alkyl ether sulfonic acid derivatives. The epoxide adducts are commonly formed by condensing the appropriate acetylenic alcohol with alkylene oxides, such as ethylene oxide, propylene oxide and epichlorohydrin. Addition agents or brighteners containing both the acetylenic linkage and the sulfonic acid group are commonly prepared by reacting the appropriate acetylenic alcohol with certain alkane sultones (such as propane sultone), or by condensing the appropriate acetylenic alcohol with a halogen-containing epoxide (such as epichlorohydrin) followed by replacement of the halogen atom with a sulfonate group.

Specific examples of these materials are shown in the following Table I. Some of the materials, e.g., A-1 and A-6 are readily available commercially while others can be prepared as described above and in more detail in the literature such as in U.S. Pat. Nos. 3,860,638 and 3,907,876. These materials represented by Formula I generally are incorporated into nickel plating baths in concentrations of from about 0.0002 to about 3.0 grams/liter and more preferably from about 0.001 to about 3.0 grams/liter.

TABLE I

| | Compound | Structure |
|---|---|---|
| A-1 | Propargyl Alcohol | $HC \equiv CCH_2OH$ |
| A-2 | Hydroxyethyl propynyl ether | $HC \equiv CCH_2OCH_2CH_2OH$ |
| A-3 | Beta-hydroxypropyl, propynyl ether | $HC \equiv CCH_2OCH_2C(CH_3)HOH$ |
| A-4 | Gamma-propynoxy, propyl sulfonic acid | $HC \equiv CCH_2O(CH_2)_3SO_3H$ |
| A-5 | Gamma-propynoxy, beta-hydroxy propyl sulfonic acid | $HC \equiv CCH_2OCH_2\underset{\underset{CH_2SO_3H}{\vert}}{C}HOH$ |
| A-6 | 2-Butyn-1,4-diol | $HOCH_2C \equiv CCH_2OH$ |
| A-7 | Bis-beta-hydroxyethyl ether 2-butyn-1,4-diol | $HOCH_2CH_2OCH_2C \equiv CCH_2OCH_2CH_2OH$ |
| A-8 | Bis-beta-hydroxypropyl ether 2-butyn-1,4-diol | $HOC(CH_3)HCH_2OCH_2C \equiv CCH_2OCH_2C(CH_3)HOH$ |

TABLE I-continued

| Compound | Structure |
| --- | --- |
| A-9  1(gamma-sulfopropoxy)-2-butyn-4-ol | HOCH₂C≡CCH₂O(CH₂)₂SO₃H |
| A-10  1,4-di(beta-hydroxy-gamma-sulfonic propoxy)-2-butyne | HO₃SCH₂            CH₂SO₃H<br>HOCHCH₂OCH₂C≡CCH₂OCH₂CHOH |

Another particular type of leveling agent which can be incorporated in the plating baths in combination with the acetylenic compositions of the invention are heterocyclic compounds having the formula $$RN^+\text{—}R'\text{—}SO_3\text{—} \qquad II$$

wherein RN is an aromatic heterocyclic nitrogen-containing group, and R' is an alkylene or hydroxy alkylene group. These compounds are referred to as sulfobetaines.

Generally, the RN group will be an aromatic nitrogen-containing group such as pyridine, substituted pyridines, quinoline, substituted quinolines, isoquinoline, substituted isoquinolines, benzimidazoles, and acridines. Various substituents can be incorporated into the aromatic nitrogen-containing groups specified above, and the substituent may be attached to the various positions of the aromatic group. Examples of substituents include hydroxy, alkoxy, halide, lower alkyl, lower alkenyl, amino alkyl, mercapto, cyano, hydroxyalkyl, acetyl, benzoyl, etc.

More particularly the sulfo-betaine compounds can be characterized by the following formula

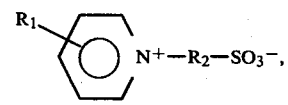

III

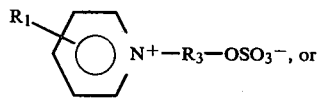

IV

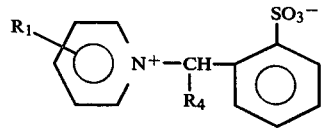

V wherein
R₁ is hydrogen, benzo(b), or one or more lower alkyl, halide, hydroxy, lower alkenyl or lower alkoxy groups,
R₂ is an alkylene or hydroxy alkylene group containing three or four carbon atoms in a straight chain,
R₃ is an alkylene or hydroxy alkylene group containing two or three carbon atoms in a straight chain, and
R₄ is a hydrogen or a hydroxyl group.

As can be seen from Formulas III, IV and V, the sulfobetaines contain a pyridinium portion which may be an unsubstituted pyridine ring or a substituted pyridine ring. Thus, R₁ may be one or more lower alkyl groups, halogen groups, lower alkoxy groups, hydroxy groups or lower alkenyl groups.

More specific examples of the pyridine groups which may be included in the above Formulas III–V include pyridine, 4-methyl pyridine (picoline), 4-ethyl pyridine, 4-t-butyl pyridine, 4-vinyl pyridine, 3-chloro pyridine, 4-chloro pyridine, 2,3 or 2,4 or 2,6 or 3,5-di-methyl pyridine, 2-methyl-5-ethyl pyridine, 3-methyl pyridine, 3-hydroxy pyridime, 2-methoxy pyridine, 2-vinyl pyridine.

In Formula III, R₂ can be an alkylene or hydroxy alkylene group containing three or four carbon atoms in a straight chain which may contain alkyl substituents which may be represented by Formula VI

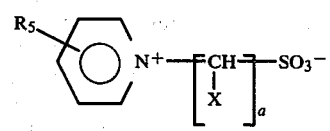

VI wherein R₅ is hydrogen or a lower alkyl group, one X is hydrogen, hydroxy or a hydroxy methyl group, the remaining X is hydrogen and a is 3 or 4.

The preparation of the sulfo-betaines of Formula III wherein R₂ is an alkylene radical is described in, for example, U.S. Pat. No. 2,876,177, which disclosure is incorporated by reference. Briefly, the compounds are formed by reaction of pyridine or a substituted pyridine with lower 1,3- or 1,4-alkyl sultones. Examples of such sultones include propane sultone and 1,3- or 1,4-butane sultone. The reaction products formed thereby are internal salts of quaternary ammonium-N-propane-omega-sulfonic acids or the corresponding butane derivative, depending on the alkyl sultone used.

The preferred examples of sulfo-betaines of Formula III wherein R₂ is an alkylene group may be represented by the following formula

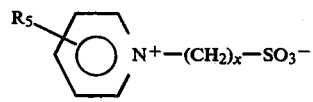

VII wherein R₅ is hydrogen, one or more lower alkyl groups or a benzo(b) group, and x is 3 or 4.

The preparation of the sulfo-betaine of Formula III wherein R₂ is a hydroxy alkylene group is described in, for example, U.S. Pat. No. 3,280,130. The method described in this patent involves a first reaction step wherein pyridine is reacted with epichlorohydrin in the presence of hydrochloric acid, and, thereafter, in a second reaction step, the quaternary salt formed thereby is reacted with sodium sulfite. The disclosure of U.S. Pat. No. 3,280,130 is incorporated by reference.

Preferred examples of the sulfo-betaines wherein R₂ is a hydroxy alkylene group including pyridine compounds of the formula

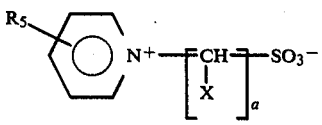

VIII wherein $R_5$ is hydrogen, one or more lower alkyl groups or a benzo(b) group, a is 3 or 4, one X substituent is a hydroxyl group and the other are hydrogen. In an alternative embodiment, two of the X groups could be hydrogen and the third X group could be a hydroxy alkyl group, preferably, a hydroxy methyl group.

The sulfo-betaines useful as brighteners in the baths of the invention include sulfo-betaines of the type represented by Formula IV above wherein $R_1$ is defined as in Formula II, and $R_3$ is an alkylene or hydroxy alkylene group containing two or three carbon atoms in a straight chain and optionally pendant hydroxyl groups, hydroxyl alkyl groups or alkyl groups containing one or two carbon atoms. Preferred examples of the betaines represented by Formula IV are those wherein $R_1$ includes pyridine compounds of the formula

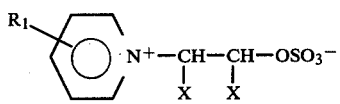

IX wherein $R_1$ is hydrogen, a lower alkyl group or a benzo(b) group, and both X groups are hydrogen or one X is hydrogen and the other is a hydroxyl group.

The preparation of the sulfo-betaines of the type represented by Formulas IV and IX which are known as pyridinium-alkane sulfate betaines is known in the art. For example, the sulfate betaines can be prepared by reacting a pyridine compound with an alkanol compound containing a halogen atom to form an intermediate hydroxylalkyl pyridinium-halide which is thereafter reacted with the corresponding halosulfonic acid to form the desired betaine. Specifically, pyridinium-(ethyl sulfate-2) betaine can be prepared by reacting ethylene chlorohydrin with pyridine followed by reaction with chlorosulfonic acid. The details of the procedure are described in U.S. Pat. No. 3,314,868 and the disclosure is hereby incorporated by reference. Other alkanol compounds containing a halogen which can be reacted with pyridine to form the desired betaines include 1-chloro-2-propanol, 3-chloro-1-propanol, etc.

The useful betaines also include those represented by Formula V given above which may be obtained by reacting, for example, o-chloro benzyl chloride (prepared from o-chloro benzaldehyde) with pyridine or a substituted pyridine followed by replacement of the o-chloro group with a sulfonic acid group. Although a similar reaction can be conducted with the corresponding meta and para chloro compounds, the ortho derivative performs best in the plating baths of the invention.

It often is desirable to include in the plating baths of this invention one or more bath-soluble complexing agents for iron which may be aliphatic carboxylic acid containing from about 1 to 3 carboxyl groups and from about 1 to 6 hydroxyl groups. The carboxy group may be present as —COOH, as the anion —COO$^-$ in solution, or in the form of an internal lactone such as present in the sugars. Suitable complexing agents of this type are in the hydroxy substituted lower aliphatic carboxylic acids having from two to eight carbon atoms such as ascorbic acid, isoascorbic acid, citric acid, malic acid, glutaric acid, gluconic acid, muconic acid, glutamic acid, glycollic acid, aspartic acid, dextrose, sucrose, etc. Amine-containing complexing agents such as nitrilotriacetic acid and ethylene diamine tetra-acetic acid also are useful. The water soluble salts of the complexing agents such as the ammonium, alkali metal and iron salts may be utilized in the baths of the invention.

The purpose of the complexing agents is to keep the metal ions, particularly the ferrous and ferric ions, in solution thereby preventing precipitation of iron as ferric hydroxide. The complexing agent generally will be incorporated into the bath in an amount ranging from about 5 to about 100 grams/liter to provide a mole ratio of complexing agent to iron ions in the bath of from about 1:1 to 50:1.

The incorporation of wetting or surface active agents (surfactants) and particularly anionic wetting agents into the plating baths of the invention, especially when brighteners are included, results in a nickel or nickel-iron plating with improved leveling and brightness, and the plating baths exhibit improved stability. The surfactants also minimize gas streaking and pitting.

Examples of the sulfonated surfactants include sodium lauryl sulfonate, sodium sulfate derivative of 2-ethyl-1-hexanol and sodium dialkyl sulfosuccinates such as the dihexyl ester of sodium sulfosuccinic acid.

The acidic plating baths of the present invention deposit a level nickel or nickel-iron plate on substrates at any conventional temperature such as from about 35° to about 70° C., but preferably between about 45° to about 60° C. The amounts of the various additive components and the length of time required for the deposition of the desired nickel plate will vary depending on the various factors such as current density and the desired depth or amount of nickel deposit.

A typical nickel plating bath may be illustrated as follows:

|  | g/l |
|---|---|
| $NiSO_4.6H_2O$ | 350 |
| $NiCl.6H_2O$ | 75 |
| Boric Acid | 45 |
| Surfactant: e.g., sodium lauryl sulfate | 0.5 |
| pH | 3.5 to 4.5 |

A low-salt nickel plating bath may be illustrated as follows:

|  | g/l |
|---|---|
| $NiSO_4.6H_2O$ | 75 |
| $NiCl_26H_2O$ | 112 |
| Boric Acid | 45 |
| pH | 3.5 to 4.5 |

A typical nickel-iron plating bath may be illustrated as follows:

|  | g/l |
|---|---|
| $NiSO_4.6H_2O$ | 300 |
| $NiCl_2.6H_2O$ | 60 |
| Boric Acid | 45 |
| Complexing agent: isoascorbic acid and/or sodium gluconate | 5<br>15 |
| $FeSO_4.7H_2O$ | 20 |
| Surfactant | 0.3 |
| pH | 4 |
| Temperature | 60° C. |

Specific examples of the acetylenic compositions of the invention which can be added to the above plating baths include the compositions prepared in Examples 1 to 6 above.

Specific examples of sulfo-betaines which can be added to the above plating baths at a concentration of about 0.25 g/l of bath are as follows:

TABLE II

| Additive No. | Identification |
|---|---|
| S-1 |  |
| S-2 |  |
| S-3 | 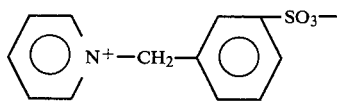 |
| S-4 | 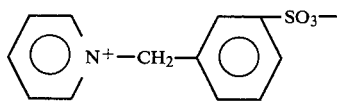 |

Specific examples of Class I brighteners used in the above-described nickel plating baths are identified in Table III.

TABLE III

| Additive No. | Identification |
|---|---|
| B-1 | sodium saccharinate |
| B-2 | o-sulfobenzaldehyde |
| B-3 | Naphthalene trisulfonic acid |
| B-4 | Sodium allyl sulfonate |

Specific examples of the plating baths of the invention are prepared by adding the above-described additive compounds to the typical nickel and nickel-iron plating baths described above. The various combinations of acetylenic composition, sulfo-betaines, and Class I brighteners and the amounts thereof incorporated into the typical and low salt plating baths are summarized in the following Tables IVA and IVB:

TABLE IVA

| Bath Example | Bath Type | Acetylene Composition of Example: g/l | Sulfo-betaine: g/l | | Brightner: g/l | |
|---|---|---|---|---|---|---|
| A | Nickel | 2 | 0.5 | S-2 | 0.25 | B-1 | 3 |
| B | Nickel | 2 | 0.8 | S-2 | 0.25 | B-3 | 3 |
| C | Nickel-iron | 3 | 0.5 | S-2 | 0.25 | B-3 | 3 |
| D | Nickel-iron | 2 | 0.5 | S-2 | 0.25 | B-1 | 3 |
| E | Nickel | 2 | 0.5 | S-3 | 0.25 | B-1 | 3 |
| F | Nickel-iron | 2 | 0.5 | S-3 | 0.25 | B-2 | 2 |
| G | Nickel | 5 | 0.05 | S-2 | 0.25 | B-1 | 3 |
| H | Nickel | 4 | 0.5 | S-2 | 0.25 | B-1 | 3 |
| I | Nickel | 6 | 0.05 | S-3 | 0.25 | B-1 | 3 |
| J | Nickel | 7 | 0.05 | S-3 | 0.25 | B-1 | 3 |

TABLE IVB

| Bath Example | Bath Type | 3-(2-propynoxy)-2-propenoic acid g/l | Sulfo-betaine g/l | Brighteners g/l | | Other Acetylenic Compound g/l | |
|---|---|---|---|---|---|---|---|
| K | Nickel | .02 | S-3 | 0.25 | B-3 | 3 | None | — |
| | | | | | B-1 | 4 | | |
| L | Low Salt Nickel | .007 | none | — | B-4 | 2 | None | — |
| M | Nickel | .002 | none | — | B-3 | 3 | Propargyl alcohol | 0.01 |
| | | | | | B-1 | 4 | | |
| N | Nickel | .002 | S-3 | 0.25 | B-3 | 3 | Propargyl alcohol | 0.01 |
| | | | | | B-1 | 4 | | |
| O | Low Salt Nickel | .002 | none | — | B-4 | 2 | Butyne-diol | 0.03 |
| P | Nickel | .002 | S-3 | 0.3 | B-1 | 3 | Butyne-diol | 0.02 |
| | | | | | B-4 | 4 | | |
| Q | Nickel | .01 | S-3 | 0.25 | B-3 | 3 | Propargyl alcohol | .001 |
| | | | | | B-1 | 4 | | |
| R | Nickel | .004 | S-4 | 0.3 | B-3 | 3 | Propargyl alcohol | 0.01 |
| | | | | | B-1 | 4 | | |

The utility of the above-described specific examples of the plating baths of the invention and the method of utilizing such baths for plating substrates is demonstrated by plating uniformly scratched brass panels in a Hull Cell at 60° C. and at 2 amperes for 15 minutes. The plating bath examples described in Table IVB produce good leveling and covering in all current density regions, high lustre, pit-free deposits, and normal plate distribution. The plating bath examples in Table IVA containing 3-(2-propynoxy)-2-propenoic acid also deposit level coating on test panels.

As mentioned above, the plating bath examples summarized in Tables IVA and IVB can be modified to include other Class I brightener compounds, Class II brightener compounds in combination with the Class I brighteners, and complexing agents such as ascorbic acid and gluconic acid to improve one or more properties of the plating baths including stability and useful plating life.

Although the above examples illustrate the utility of the nickel and nickel-iron plating baths of the invention for depositing a nickel plate and nickel-iron alloy on brass, the electroplating baths of the invention may be utilized on all types of metals and alloys, for example, on iron, zinc die cast, copper and brass, and the plating baths may be employed in all types of industrial nickel and nickel-iron plating processes including barrel plating.

In practice, the improved nickel and nickel-iron plating baths of the invention may be operated on a continuous or intermittent basis, and from time to time, the components of the bath have to be replenished. The various components may be added singly as required or may be added in combination. The amounts of the various additive compositions to be added to the plating baths may be varied over a wide range depending on the nature and the performance of the nickel plating bath to which the composition is added. Such amounts can be determined readily by one skilled in the art.

Another aspect of this invention relates to additive compositions which are concentrates of bath components which may be dissolved or dispersed in water. The additive compositions of the invention will comprise various combinations of the 3-(2-propynoxy)-2-propenoic acid or acetylenic compositions of the invention, with or without the sulfo-betaines, with or without the Class I brightener, and may contain any other desirable plating bath additives described above. The amounts of the propenoic acid or acetylenic compositions, sulfo-betaines, and/or Class I brightener agents included in the additive compositions of the invention will be such that when they are diluted or added to a plating bath, they will provide the requisite amounts of the components in the bath or the requisite amounts of the components required to replenish the bath.

The following additive compositions or concentrates illustrate the various combinations of compounds that may be prepared and utilized in accordance with the invention for preparing or maintaining the nickel and nickel-iron plating baths of the invention and/or improving the performance of the baths. In the following compositions, the identification of the additives can be determined from the identifications given for the additives in Tables II and III.

|  | Parts by Weight |
|---|---|
| Additive Composition 1 | |
| 3-(2-propynoxy)-2-propenoic acid | 10 |
| S-3 | 100 |
| B-1 | 150 |
| B-3 | 100 |
| Water | 640 |
| Additive Composition 2 | |
| 3-(2-propynoxy)-2-propenoic acid | 10 |
| propargyl alcohol | 50 |
| B-1 | 60 |
| S-3 | 20 |
| Ascorbic acid | 60 |
| Water | 300 |
| Additive Composition 3 | |
| Product of Example 2 | 25 |
| S-1 | 50 |
| B-2 | 150 |
| Water | 275 |
| Additive Composition 4 | |
| Product of Example 2 | 50 |
| S-3 | 40 |
| B-2 | 150 |
| Water | 770 |
| Additive Composition 5 | |
| Product of Example 2 | 50 |
| S-3 | 25 |
| B-3 | 100 |
| Water | 815 |
| Additive Composition 6 | |
| Product of Example 2 | 25 |
| S-2 | 40 |
| Sodium allyl sulfonate | 100 |
| Water | 200 |
| Additive Composition 7 | |
| Product of Example 2 | 20 |
| S-3 | 20 |
| B-1 | 60 |
| Ascorbic acid | 60 |
| Water | 340 |
| Additive Composition 8 | |
| Product of Example 5 | 5 |
| S-1 | 50 |
| B-2 | 150 |
| Water | 295 |
| Additive Composition 9 | |
| Product of Example 5 | 5 |
| S-3 | 25 |
| B-3 | 100 |
| Water | 370 |
| Additive Composition 10 | |
| 3-(2-propynoxy)-2-propenoic acid | 10 |
| Butynediol | 50 |
| B-1 | 60 |
| S-3 | 20 |
| Water | 360 |

I claim:

1. 3-(2-propynoxy)-2-propenoic acid.

2. A method of preparing 3-(2-propynoxy)-2-propenoic acid which comprises reacting propiolic acid with propargyl alcohol in an aqueous alkaline solution and thereafter acidifying the reaction mixture.

3. The method of claim 2 wherein the alkaline solution is a solution of alkali or alkaline earth metal base in water.

4. An acetylenic composition prepared by a process comprising the steps of
   (a) reacting propargyl alcohol with an alkali metal permanganate in an aqueous alkaline solution,
   (b) filtering the reaction mixture, and
   (c) acidifying the filtrate with acid.

5. The composition of claim 4 wherein the permanganate is potassium permanganate.

6. The composition of claim 4 wherein the aqueous alkaline solution comprises a solution of sodium or potassium hydroxide in water.

7. The composition of claim 4 wherein the filtrate is acidified with sulfuric acid to a pH of less than about 2.

8. An acetylenic composition prepared by the process comprising the steps of
   (a) reacting about 1.5 parts of propargyl alcohol with about 0.1 to about 1.0 part of potassium permanganate in an aqueous alkaline solution at a pH of from about 9 to 11,
   (b) filtering the reaction mixture, and
   (c) acidifying the filtrate with acid to a pH less than about 2.

9. An aqueous acidic plating bath for the electrodeposition of nickel or a nickel-iron alloy on a substrate which bath comprises nickel ions, or a mixture of nickel ions and iron ions, and as a brightening and leveling agent, an effective amount of 3-(2-propynoxy)-2-propenoic acid.

10. The bath of claim 9 also including a secondary brightener of the formula $$R_1C{\equiv}CCH_2OR_2 \qquad I$$

wherein $R_1$ is selected from H, $CH_2OH$, $CH_2OR_2$; $R_2$ is selected from H, $(CH_2CH_2O)_nH$, $(CH_2CH(OH)CH_2)_nH$, $(CH_2)_mSO_3M$, $(CH_2CH(OH)CH_2)_n\text{-}SO_3M$, $(CH_2CH_2O)_n(CH_2CH(OH)CH_2)SO_3M$, and $(CH_2CH_2O)_n(CH_2)_mSO_3M$, where n is an integer from 1 to 10; m is an integer from 1 to 4; and M is selected from hydrogen, ammonium, alkali metal, nickel and cobalt.

11. The bath of claim 10 wherein $R_1$ is hydrogen or hydroxymethyl.

12. The bath of claim 10 also containing at least one surfactant or wetting agent.

13. The bath of claim 10 also containing at least one heterocyclic leveling compound having the general formula

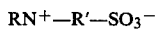   II wherein RN is an aromatic heterocyclic nitrogen-containing group and R' is an alkylene or hydroxy alkylene group.

14. The plating bath of claim 13 wherein the heterocyclic leveling compound is at least one sulfo-betaine having the general formula

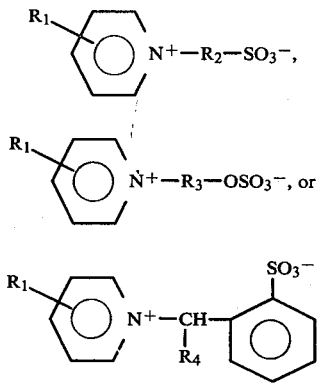

wherein
  $R_1$ is hydrogen, benzo(b), one or more lower alkyl, halide, hydroxy, lower alkenyl or lower alkoxy groups or benzo(b) groups substituted with one or more lower alkyl, halide, hydroxy, lower alkenyl or lower alkoxy groups,
  $R_2$ is an alkylene or hydroxy alkylene group containing three or four carbon atoms in a straight chain,
  $R_3$ is an alkylene or hydroxy alkylene group containing two or three carbon atoms in a straight chain, and
  $R_4$ is hydrogen or a hydroxyl group.

15. The plating bath of claim 9 wherein the 3-(2-propynoxy)-2-propenoic acid is present in an amount of from about 0.001 to 0.05 gram per liter.

16. An aqueous acidic plating bath for the electrodeposition of nickel or a nickel-iron alloy on a substrate which bath comprises nickel ions or a mixture of nickel ions and iron ions, and as a brightening and leveling agent, an effective amount of an acetylenic composition of any one of claims 4–8.

17. The bath of claim 16 also including at least one surfactant or wetting agent.

18. The plating bath of claim 16 wherein the bath contains a mixture of nickel ions and iron ions and at least one bath-soluble complexing agent for iron which is an aliphatic carboxylic acid containing from 1 to 3 carboxyl groups and from about 1 to 6 hydroxyl groups.

19. The plating bath of claim 16 wherein the bath also contains at least one heterocyclic leveling compound having the general formula

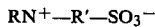   II wherein RN is an aromatic heterocyclic nitrogen-containing group and R' is an alkylene or hydroxy alkylene group.

20. The plating bath of claim 19 wherein the heterocyclic leveling compound is at least one sulfo-betaine having the general formula

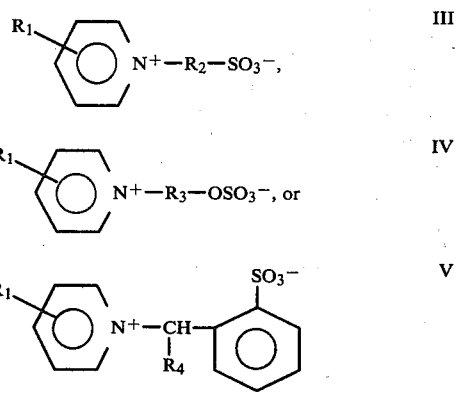

wherein
  $R_1$ is hydrogen, benzo(b), one or more lower alkyl, halide, hydroxy, lower alkenyl or lower alkoxy groups or benzo(b) groups substituted with one or more lower alkyl, halide, hydroxy, lower alkenyl or lower alkoxy groups,
  $R_2$ is an alkylene or hydroxy alkylene group containing three or four carbon atoms in a straight chain,
  $R_3$ is an alkylene or hydroxy alkylene group containing two or three carbon atoms in a straight chain, and
  $R_4$ is hydrogen or a hydroxyl group.

21. The plating bath of claim 20 wherein the sulfobetaine compound is represented by Formula III and $R_1$ is hydrogen.

22. The plating bath of claim 20 wherein the sulfobetaine is present in an amount of from about 0.1 to about 10 grams per liter of bath.

23. The plating bath of claim 16 wherein the acetylenic composition is present in the plating bath in an amount of from about 0.001 to about 1.0 gram per liter.

24. The plating bath of claim 16 wherein the bath also contains from about 0.5 to about 25 grams per liter of at least one brightener selected from the group consisting of an aliphatic or aromatic sulfonamide, sulfonimide, sulfonic acid or the bath-soluble salts thereof.

25. The method of electrodepositing a nickel or nickel-iron alloy on a substrate which comprises electroplating said substrate in an aqueous acidic bath of claim 16.

26. An aqueous acidic plating bath for electrodepositing nickel on a substrate, which bath comprises
  (a) from about 5 to about 350 grams per liter of nickel ions,
  (b) from about 0.01 to about 1.0 gram of the acetylenic composition of any one of claims 1-8,
  (c) at least one sulfo-betaine having the general formula

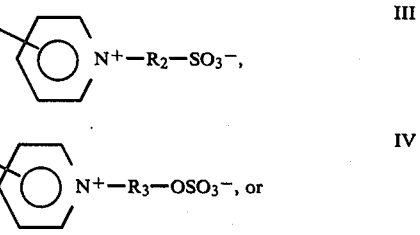

-continued

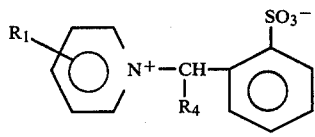 V wherein
R₁ is hydrogen, benzo(b), one or more lower alkyl, halide, hydroxy, lower alkenyl or lower alkoxy groups or benzo(b) groups substituted with one or more lower alkyl, halide, hydroxy, lower alkenyl or lower alkoxy groups, R₂ is an alkylene or hydroxy alkylene group containing three or four carbon atoms in a straight chain, R₃ is an alkylene or hydroxy alkylene group containing two or three carbon atoms is a straight chain, and R₄ is hydrogen or a hydroxyl group, and (d) from about 0.5 to about 25 grams per liter of a brightener selected from the group consisting of an aliphatic or aromatic sulfonamide, sulfonimide, sulfonic acid or bath-soluble salts thereof.

27. The plating bath of claim 26 wherein R₁ in Formulas III, IV and V is a hydrogen atom.

28. A method of electrodepositing nickel on a substrate which comprises electroplating said substrate with the aqueous acidic plating bath of claim 25.

29. An additive composition for plating baths useful for electrodepositing of nickel or a nickel-iron alloy on a substrate comprising a mixture of (a) the acetylenic composition of any one of claims 1-8, (b) at least one sulfo-betaine having the general formula

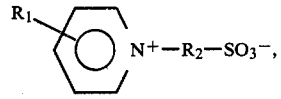 III

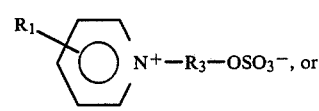 IV

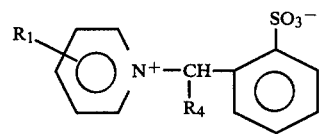 V wherein
R₁ is hydrogen, benzo(b), one or more lower alkyl, halide, hydroxy, lower alkenyl or lower alkoxy groups or benzo(b) groups substituted with one or more lower alkyl, halide, hydroxy, lower alkenyl or lower alkoxy groups, R₂ is an alkylene or hydroxy alkylene group containing three or four carbon atoms in a straight chain, R₃ is an alkylene or hydroxy alkylene group containing two or three carbon atoms in a straight chain, and R₄ is hydrogen or a hydroxyl group.

30. The additive composition of claim 29 also containing at least one aliphatic or aromatic sulfonamide, sulfonimide, sulfonic acid or bath-soluble salt thereof.

31. The additive composition of claim 29 also containing at least one bath-soluble complexing agent which is an aliphatic carboxylic acid containing from about 1 to 3 carboxyl groups and from about 1 to about 7 hydroxyl groups.

32. The additive composition of claim 29 wherein the acetylenic composition is 3-(2-propynoxy)-2-propenoic acid and the bath also contains propargyl alcohol or butynediol.

* * * * *